(12) United States Patent
Sha

(10) Patent No.: US 11,457,834 B2
(45) Date of Patent: Oct. 4, 2022

(54) SYSTEM AND METHOD FOR GENERATING ECG REFERENCE DATA FOR MR IMAGING TRIGGERING

(71) Applicant: General Electric Company, Schenectady, NY (US)

(72) Inventor: Liewei Sha, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 431 days.

(21) Appl. No.: 16/041,484

(22) Filed: Jul. 20, 2018

(65) Prior Publication Data
US 2020/0022608 A1   Jan. 23, 2020

(51) Int. Cl.
*A61B 5/055* (2006.01)
*A61B 5/352* (2021.01)
(Continued)

(52) U.S. Cl.
CPC .............. *A61B 5/055* (2013.01); *A61B 5/352* (2021.01); *A61B 5/7225* (2013.01); *A61B 5/316* (2021.01);
(Continued)

(58) Field of Classification Search
CPC ..... A61B 5/055; A61B 5/0456; A61B 5/7225; A61B 5/0472; A61B 5/7257;
(Continued)

(56) References Cited

U.S. PATENT DOCUMENTS

| | | | |
|---|---|---|---|
| 4,712,560 | A | 12/1987 | Schaefer et al. |
| 4,865,043 | A | 9/1989 | Shimoni |

(Continued)

FOREIGN PATENT DOCUMENTS

| | | |
|---|---|---|
| CN | 101843482 B | 11/2013 |
| CN | 108125678 A * | 6/2018 |

(Continued)

OTHER PUBLICATIONS

Jon M. Chia et al., Performance of QRS Dectection for Cardiac Magnetic Resonance Imaging with a Novel Vectorcardiographic Triggering Method, Journal of Magnetic Resonance Imaging, 2000, pp. 678-688, vol. 12, Publisher: Wiley-Liss, inc.

(Continued)

*Primary Examiner* — Catherine B Kuhlman
*Assistant Examiner* — Nicholas A Robinson
(74) *Attorney, Agent, or Firm* — Andrus Intellectual Property Law, LLP

(57) ABSTRACT

A method of generating ECG reference data for MR image data acquisition includes obtaining an initial ECG dataset from a patient prior to moving the patient into a bore of the MRI device, wherein the initial ECG dataset comprises at least two channels of ECG data. An initial set of R-peaks is identified and an initial R-peak polarity and initial R-R interval are determined. A reference ECG dataset is then obtained from the patient once the patient is in the bore of the MRI device. A reference set of R-peaks is identified in the reference ECG dataset based on the initial R-peak polarity and the initial R-R interval, and R-peak reference data is generated based on the reference set of R-peaks. Acquisition of MR image data from the subject is then triggered using the R-peak reference data.

12 Claims, 10 Drawing Sheets

(51) Int. Cl.
*A61B 5/35* (2021.01)
*A61B 5/316* (2021.01)
*A61B 5/361* (2021.01)
*A61B 5/366* (2021.01)
*A61B 5/00* (2006.01)
*G01R 33/567* (2006.01)

(52) U.S. Cl.
CPC ............. *A61B 5/35* (2021.01); *A61B 5/361* (2021.01); *A61B 5/366* (2021.01); *A61B 5/7203* (2013.01); *A61B 5/7257* (2013.01); *A61B 5/7289* (2013.01); *G01R 33/5673* (2013.01)

(58) Field of Classification Search
CPC ............. A61B 5/04525; A61B 5/7289; A61B 5/04017; A61B 5/7203; A61B 5/046; A61B 5/7285; A61B 5/04012; A61B 5/7221; A61B 5/0044; A61B 5/7264; A61B 5/7292; A61B 5/0402; A61B 5/7267; A61B 2576/023; G16H 50/20; G01R 33/5673
See application file for complete search history.

(56) References Cited

U.S. PATENT DOCUMENTS

| | | | |
|---|---|---|---|
| 5,052,398 A | 10/1991 | Gober | |
| 5,987,348 A | 11/1999 | Fischer et al. | |
| 6,070,097 A * | 5/2000 | Kreger | A61B 5/055 600/521 |
| 6,501,979 B1 | 12/2002 | Manning et al. | |
| 7,738,943 B2 | 6/2010 | Sha et al. | |
| 8,332,023 B2 | 12/2012 | Frank | |
| 2002/0188211 A1 | 12/2002 | Voith | |
| 2003/0088174 A1 | 5/2003 | Sussman et al. | |
| 2004/0073124 A1 | 4/2004 | Axel | |
| 2004/0102710 A1 * | 5/2004 | Kim | G06F 17/17 600/509 |
| 2007/0055145 A1 * | 3/2007 | Zelnik | A61B 6/04 600/428 |
| 2007/0135863 A1 * | 6/2007 | Gunderson | A61B 5/35 607/59 |
| 2007/0255150 A1 * | 11/2007 | Brodnick | A61B 5/352 600/509 |
| 2008/0139926 A1 * | 6/2008 | Frank | A61B 5/7285 600/413 |
| 2010/0191134 A1 * | 7/2010 | Frank | A61B 5/7285 600/521 |
| 2010/0217113 A1 * | 8/2010 | Jenkins | G01R 33/28 600/411 |
| 2013/0085405 A1 * | 4/2013 | Bera | A61B 5/0006 600/515 |
| 2013/0165805 A1 * | 6/2013 | Lee | A61B 5/316 600/521 |
| 2016/0000350 A1 * | 1/2016 | Zhang | A61B 5/352 600/512 |
| 2016/0045136 A1 * | 2/2016 | Siejko | A61N 1/3987 600/510 |
| 2016/0106332 A1 * | 4/2016 | Takeshima | A61B 5/366 600/509 |
| 2016/0120434 A1 * | 5/2016 | Park | A61B 5/4839 600/301 |
| 2016/0128643 A1 * | 5/2016 | Yoshida | A61B 5/352 600/413 |
| 2016/0198969 A1 * | 7/2016 | Cheng | A61B 5/349 600/515 |
| 2018/0028078 A1 * | 2/2018 | Gregroy | A61B 5/029 |
| 2018/0220915 A1 * | 8/2018 | Takeshima | A61B 5/366 |
| 2018/0344261 A1 * | 12/2018 | Yoshida | A61B 5/349 |
| 2019/0246966 A1 * | 8/2019 | Friedman | A61B 5/14546 |
| 2021/0267472 A1 * | 9/2021 | Yaniv | A61B 5/366 |

FOREIGN PATENT DOCUMENTS

| | | | | |
|---|---|---|---|---|
| EP | 1886625 A1 * | 2/2008 | ......... A61B 5/04012 |
| JP | 2016093488 A | 5/2016 | |

OTHER PUBLICATIONS

Van K. Daskalov et al., Developments in ECG Acquisition, Pre-processing, Parameter Measurement, and Recording, IEEE Engineering in Medicine and Biology, Mar./Apr. 1998, pp. 50-58, vol. 0739-5175, No. 98.

Stefan E. Fischer et al.. Novel Real-Time R-Wave Detection Algorithm Based on teh Vectorcardiogram for Accurate Gated Magnetic Resonance Acquisitions, Magnetic Resonance in Medicine, 1999, pp. 361-370, vol. 42, Published: Wiley-Liss, Inc.

Gary M. Friesen et al., A Comparison of the Noise Sensitivity of Nine QRS Detection Algorithms, IEEE Transactions on Biomedical Engineering, Jan. 1990, pp. 85-98, vol. 37, No. 1.

CN patent application 201910616391.2 filed Jul. 9, 2019—Office Action dated Jun. 30, 2021; 10 pages.

CN application 201910616391.2 filed Jul. 9, 2019—2nd Office Action dated Mar. 3, 2022.

JP2016093488 English Abstract; Espacenet.com search Mar. 30, 2022; 1 page.

* cited by examiner

SYSTEM AND METHOD FOR GENERATING ECG REFERENCE DATA FOR MR IMAGING TRIGGERING

BACKGROUND

The present invention relates generally to magnetic resonance (MR) imaging and, more particularly, to a system and method for generating electrocardiogram (ECG) reference data for MR image triggering.

Magnetic resonance (MR) imaging is often used to obtain internal physiological information of a patient, including for cardiac imaging. In cardiac imaging, it is typically desirable to obtain an image at a particular point in a variable cycle, such as a peak of the variable cycle, to analyze behavior during that peak. Gating is an option for characterizing different attributes of an organ for imaging. The most common techniques of gating include cardiac, respiratory, and peripheral pulse gating, and these types of gating have uses in numerous medical applications across diagnostic modalities such as CT, MR, x-ray, ultrasound, and position emission tomography (PET). Cardiac gating, for example, is an essential component of cardiac imaging while using imaging modalities such as CT and MR to minimize motion-related artifacts.

In MR imaging, when a substance such as human tissue is subjected to a uniform magnetic field (polarizing field $B_0$), the individual magnetic moments of the spins in the tissue attempt to align with this polarizing field, but precess about it in random order at their characteristic Larmor frequency. If the substance, or tissue, is subjected to a magnetic field (excitation field $B_1$) which is in the x-y plane and which is near the Larmor frequency, the net aligned moment, or "longitudinal magnetization", Mz, may be rotated, or "tipped", into the x-y plane to produce a net transverse magnetic moment Mt. A signal is emitted by the excited spins after the excitation signal $B_1$ is terminated and this signal may be received and processed to form an image.

When utilizing these signals to produce images, magnetic field gradients ($G_x$, $G_y$, and $G_z$) are employed. Typically, the region to be imaged is scanned by a sequence of measurement cycles in which these gradients vary according to the particular localization method being used. The resulting set of received NMR signals are digitized and processed to reconstruct the image using reconstruction techniques.

Magnetic resonance imaging is a diagnostic imaging technique commonly used to review, identify, and diagnose pathologies or abnormalities in a scan subject, e.g., medical patient. For example, MR images of the cardiac region are often used by health care professionals to diagnose medical conditions. Traditional MR evaluations of the cardiac region often rely on repeated cardiac-gated acquisition of MR data in order to reduce image degradation resulting from the continuous movement of the cardiac region due to respiratory and/or circulatory physiological functions.

To achieve a cardiac-gated acquisition of MR data, systems have been developed that rely on detection of a particular point in the motion cycle as a trigger to repeatedly acquire data at approximately the same phase of the motion cycle. An electrocardiogram (ECG) is generally utilized to monitor the cardiac cycle and identify a particular peak, often an R-peak, within the ECG waveform. By identifying an occurrence of the R-peak, these systems infer that a Q-peak and S-peak are associated with the R-peak and thereby identify an occurrence of a QRS complex. The identification of a QRS complex is then used as a point for triggering the acquisition of MR data from the subject to be imaged.

However, the R-peak can often be distorted or obscured by strong noise associated with MR environments. For example, spikes may be induced within the ECG waveform by RF pulses or gradient pulses and may be misidentified as an R-peak. Accordingly, such systems may infer the spike as an R-pulse of a QRS complex and mistrigger imaging. Furthermore, abnormal patient conditions such as premature ventricular contraction (PVC) may hinder detection of an R-peak. Accordingly, many identification systems may cause imaging to be triggered prematurely or fail to trigger entirely thereby degrading the image quality and extending scan durations.

SUMMARY

This Summary is provided to introduce a selection of concepts that are further described below in the Detailed Description. This Summary is not intended to identify key or essential features of the claimed subject matter, nor is it intended to be used as an aid in limiting the scope of the claimed subject matter.

In one embodiment, a method of generating ECG reference data for MR image data acquisition includes obtaining an initial ECG dataset from a patient prior to moving the patient into a bore of the MRI device, wherein the initial ECG dataset comprises at least two channels of ECG data. An initial set of R-peaks is identified, along with initial R-peak characteristics. A reference ECG dataset is then obtained from the patient once the patient is in the bore of the MRI device. A reference set of R-peaks is identified in the reference ECG dataset based on the initial R-peak characteristics, and R-peak reference data is generated based on the reference set of R-peaks. Acquisition of MR image data from the subject is then triggered using the R-peak reference data.

In one embodiment, a system for generating ECG reference data for MR image data acquisition with an MRI device, the MRI device having a core and a table moveable to move the patient in and out of the core, includes an ECG acquisition system configured to obtain at least two channels of ECG data from a patient, and an R-peak detection module executable on a processor and configured to obtain both an initial ECG dataset and a reference ECG dataset from a patient in order to generate R-peak reference data for triggering MR image data acquisition. The R-peak detection module is configured to obtain an initial ECG dataset from a patient on the table prior to moving the patient into the bore of the MRI device, wherein the initial ECG dataset comprises at least two channels of ECG data. An initial set of R-peaks are identified, and initial R-peak characteristics are determined for at least one of the at least two channels of ECG data in the initial ECG dataset. A reference ECG dataset is then obtained from the patient once the patient is in the bore of the MRI device, wherein the reference ECG dataset also comprises the at least two channels of ECG data. A reference set of R-peaks are identified in the reference ECG dataset based on the initial R-peak characteristics. R-peak reference data is then generated based on the reference set of R-peaks, wherein the R-peak reference data is formatted for use in triggering MR data acquisition.

Various other features, objects and advantages of the invention will be made apparent from the following description taken together with the drawings.

BRIEF DESCRIPTION OF THE DRAWINGS

The drawings illustrate the best mode presently contemplated of carrying out the disclosure. In the drawings.

DETAILED DESCRIPTION

Figure 1:
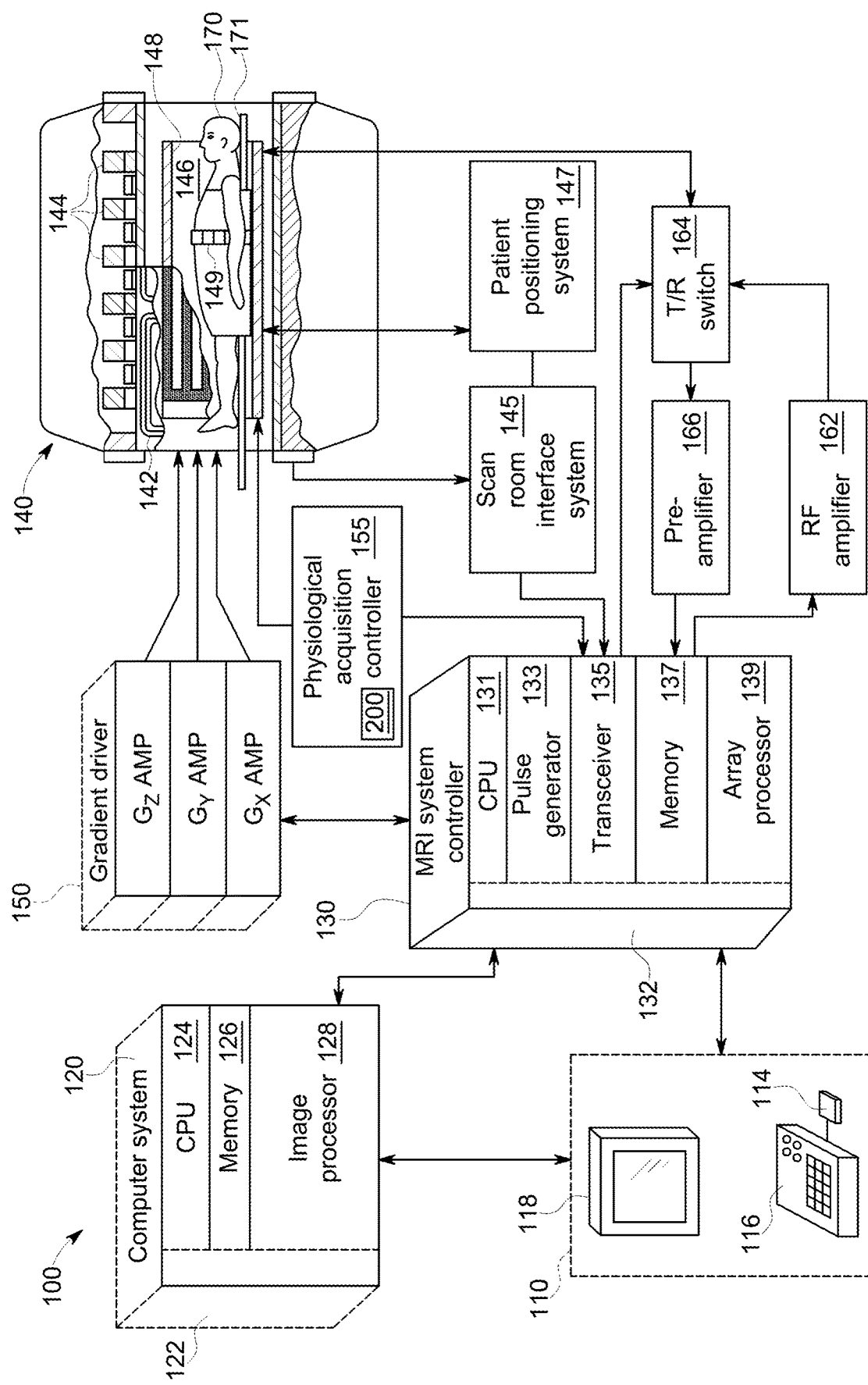
FIG. 1 is a schematic diagram of an exemplary MRI system in accordance with one embodiment of the present disclosure.

Accurate ECG R-peak reference is critical to reliably detect cardiac trigger during MR scans to overcome gradient, RF, body coil switch interference and obtain good image quality (IQ). The difficulty in obtaining accurate ECG R-peak reference is due in part to variance of ECG waveform characteristics related to a patient's underlying disease, such as atrial fibrillation (AF), premature ventricular contractions (PVC), bundle branch block (BBB), atrial and ventricular hypertrophy. In addition to the physiological barriers to R-peak detection, interference due to magnetohydrodyamic (MHD) effects, gradient, RF, and body coil switch interference, as well as table motion and patient motion, affect the ECG signals and introduce interference that decreases the signal to noise ratio (SNR) and makes R-peak detection more difficult. Such interference in the ECG waveform affects the accuracy of MR image triggering and ultimately degrades the image quality of the MR image.

Prior art R-peak detection methods are unnecessarily burdensome and introduce error and inconsistency to R-peak detection because they require an operator to manually control ECG reference data acquisition. Manually controlling the ECG reference data acquisition for R-peak detection can be problematic and burdensome because it adds overhead to the operator's work flow and may be executed insufficiently or suboptimally, such as due to operator error or lack of oversight by a clinician to adequately avoid excess interference due to scans, table motion, patient motion, etc.

Furthermore, prior R-peak detection methods and systems provide suboptimal R-peak reference data that does not account for the consistent distortion effects on the ECG data caused by the MRI system, including the MHD effects. ECG data measured inside the bore, although heavily influenced by artifact, can provide better R-peak reference data than that produced based on ECG data measured outside of the bore. This is because the R-peak reference data from inside the bore takes into consideration certain distortions on the ECG waveforms caused by the MRI system, including accounting for distortion effects of MHD caused by the strong magnetic field in the imaging environment. These effects present in the reference ECG data and in the ECG data measured during the scan, and thus accounting for the distortion effects in the R-peak reference data improves R-peak detection accuracy for ECG-based image triggering during the scan.

Method and system disclosed herein for generating ECG reference data for MR image data acquisition improves accuracy of R-peak detection and automatically generates reliable R-peak reference data. The clinical work flow is improved due to elimination of manual start and review of the acquisition process for the ECG R-peak reference data. Moreover, reliability of the automatically generated R-peak reference data is increased because MHD effects are accounted for. Thereby, issues relating to poor image quality due to incorrect ECG triggering are significantly reduced.

The disclosed system obtains an initial ECG dataset, including at least two channels of ECG data, when the patient is on the table of the MRI device but outside of the bore of the MRI device. Thus the initial ECG dataset is acquired prior to moving the patient into the bore of the MRI device. A second ECG dataset, a reference ECG dataset, is then acquired from the patient once the patient is positioned within the bore of the MRI device, wherein the reference ECG dataset is preferably obtained after completion of table movement and prior to starting the MRI scan. Thereby, interference due to table and patient motion and other motion by the MRI device are minimized. Yet, by acquiring the reference ECG dataset once the patient is positioned within the bore, the consistent effects of the MR environment on the ECG waveforms can be accounted for in the reference data, including the MHD effect. The reference ECG dataset obtained in the bore will contain significantly more noise than the initial dataset obtained outside of the bore, and R-peak detection will be more difficult. In order to address this issue, information gained from the initial ECG dataset is utilized to assist in R-peak detection for the reference ECG dataset. Initial R-peak characteristics are determined—such as an initial R-peak polarity and initial R-R interval—preferably for each of the channels of the initial ECG dataset. The R-peak detection algorithm then utilizes the information learned from the initial dataset to improve R-peak detection for the reference ECG dataset. The initial R-peak characteristic information is used for R-peak detection in the noisier reference ECG dataset for each corresponding channel. Thereby, R-peak detection is improved and generation of accurate and reliable R-peak reference data is accomplished for use in triggering acquisition of MR image data. Further details and explanation of exemplary embodiments is provided below.

Referring to FIG. 1, a schematic diagram of an exemplary MRI system 100 is shown in accordance with an embodiment. The operation of MRI system 100 is controlled from an operator workstation 110 that includes an input device 114, a control panel 116, and a display 118. The input device 114 may be a joystick, keyboard, mouse, track ball, touch activated screen, voice control, or any similar or equivalent input device. The control panel 116 may include a keyboard, touch activated screen, voice control, buttons, sliders, or any similar or equivalent control device. The operator workstation 110 is coupled to and communicates with a computer system 120 that enables an operator to control the production and viewing of images on display 118. The computer system 120 includes a plurality of components that communicate with each other via electrical and/or data connections 122. The computer system connections 122 may be direct wired connections, fiber optic connections, wireless communication links, or the like. The components of the computer system 120 include a central processing unit (CPU) 124, a memory 126, which may include a frame buffer for storing image data, and an image processor 128. In an alternative embodiment, the image processor 128 may be replaced by image processing functionality implemented in the CPU 124. The computer system 120 may be connected to archival media devices, permanent or back-up memory storage, or a network. The computer system 120 is coupled to and communicates with a separate MRI system controller 130.

The MRI system controller 130 includes a set of components in communication with each other via electrical and/or data connections 132. The MRI system controller connections 132 may be direct wired connections, fiber optic connections, wireless communication links, or the like. The components of the MRI system controller 130 include a CPU 131, a pulse generator 133, which is coupled to and communicates with the operator workstation 110, a transceiver 135, a memory 137, and an array processor 139. In an alternative embodiment, the pulse generator 133 may be integrated into a resonance assembly 140 of the MRI system 100. The MRI system controller 130 is coupled to and receives commands from the operator workstation 110 to indicate the MRI scan sequence to be performed during a MRI scan. The MRI system controller 130 is also coupled to and communicates with a gradient driver system 150, which is coupled to a gradient coil assembly 142 to produce magnetic field gradients during a MRI scan.

The pulse generator 133 may also receive data from a physiological acquisition controller 155 that receives signals from a plurality of different sensors connected to an object or patient 170 undergoing a MRI scan, including electrocardiography (ECG) signals from electrodes attached to the patient 170. And finally, the pulse generator 133 is coupled to and communicates with a scan room interface system 145, which receives signals from various sensors associated with the condition of the resonance assembly 140. The scan room interface system 145 is also coupled to and communicates with a patient positioning system 147, which sends and receives signals to control movement of a table 171. The table 171 is controllable to move the patient in and out of the bore 146 and to move the patient to a desired position within the bore 146 for a MRI scan.

The MRI system controller 130 provides gradient waveforms to the gradient driver system 150, which includes, among others, $G_x$, $G_y$, and $G_z$ amplifiers. Each $G_x$, $G_y$, and $G_z$ gradient amplifier excites a corresponding gradient coil in the gradient coil assembly 142 to produce magnetic field gradients used for spatially encoding MR signals during a MRI scan. The gradient coil assembly 142 is included within the resonance assembly 140, which also includes a superconducting magnet having superconducting coils 144, which in operation, provides a homogenous longitudinal magnetic field $B_0$ throughout a bore 146, or open cylindrical imaging volume, that is enclosed by the resonance assembly 140. The resonance assembly 140 also includes a RF body coil 148 which in operation, provides a transverse magnetic field $B_1$ that is generally perpendicular to $B_0$ throughout the bore 146. The resonance assembly 140 may also include RF surface coils 149 used for imaging different anatomies of a patient undergoing a MRI scan. The RF body coil 148 and RF surface coils 149 may be configured to operate in a transmit-and-receive mode, transmit mode, or receive mode.

An object or patient 170 undergoing a MRI scan may be positioned within the bore 146 of the resonance assembly 140. The transceiver 135 in the MRI system controller 130 produces RF excitation pulses that are amplified by an RF amplifier 162 and provided to the RF body coil 148 and RF surface coils 149 through a transmit/receive switch (T/R switch) 164.

As mentioned above, RF body coil 148 and RF surface coils 149 may be used to transmit RF excitation pulses and/or to receive resulting MR signals from a patient undergoing a MRI scan. The resulting MR signals emitted by excited nuclei in the patient undergoing a MRI scan may be sensed and received by the RF body coil 148 or RF surface coils 149 and sent back through the T/R switch 164 to a pre-amplifier 166. The amplified MR signals are demodulated, filtered and digitized in the receiver section of the transceiver 135. The T/R switch 164 is controlled by a signal from the pulse generator 133 to electrically connect the RF amplifier 162 to the RF body coil 148 during the transmit mode and connect the pre-amplifier 166 to the RF body coil 148 during the receive mode. The T/R switch 164 may also enable RF surface coils 149 to be used in either the transmit mode or receive mode. The resulting MR signals sensed and received by the RF body coil 148 are digitized by the transceiver 135 and transferred to the memory 137 in the MRI system controller 130.

A MR scan is complete when an array of raw k-space data, corresponding to the received MR signals, has been acquired and stored temporarily in the memory 137 until the data is subsequently transformed to create images. This raw k-space data is rearranged into separate k-space data arrays for each image to be reconstructed, and each of these separate k-space data arrays is input to the array processor 139, which operates to Fourier transform the data into arrays of image data.

The array processor 139 uses a known transformation method, most commonly a Fourier transform, to create images from the received MR signals. These images are communicated to the computer system 120 where they are stored in memory 126. In response to commands received from the operator workstation 110, the image data may be archived in long-term storage or it may be further processed by the image processor 128 and conveyed to the operator workstation 110 for presentation on the display 118. In various embodiments, the components of computer system 120 and MRI system controller 130 may be implemented on the same computer system or a plurality of computer systems.

Figure 2A:
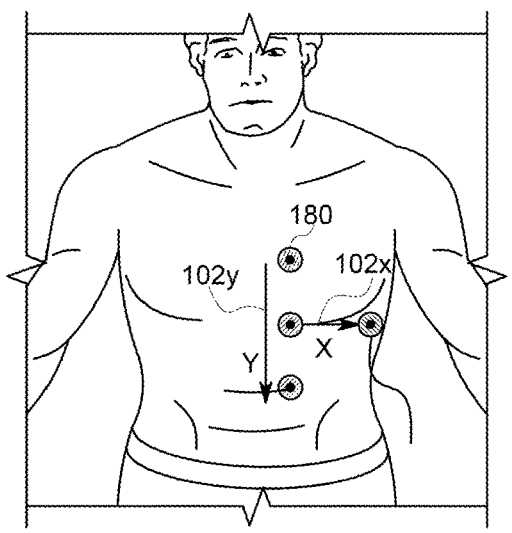
FIGS. 2A-2C illustrate exemplary ECG electrode arrangements on a patient for obtaining ECG data in accordance with embodiments of the present disclosure.
Figure 2B:
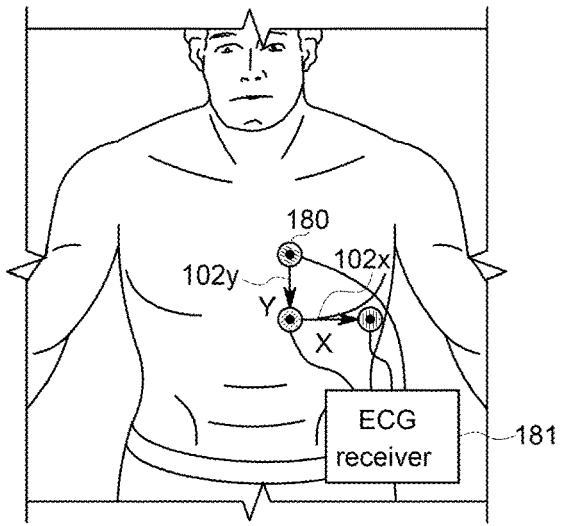
Figure 2C:
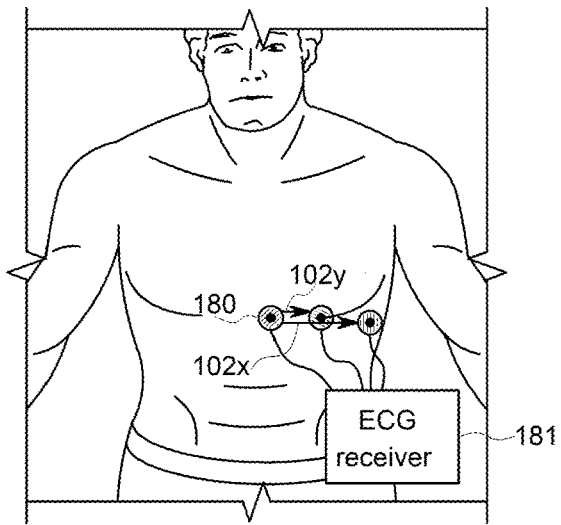

Referring to FIGS. 2A-2C, exemplary ECG electrode arrangements on a patient for obtaining ECG data are shown in accordance with embodiments of the present disclosure. ECG data is acquired and provided to the physiological acquisition controller 155 for use by the system 100. FIGS. 2A-2C depict exemplary arrangements of electrodes 180 on the patient to obtain two channels of ECG date. While various lead configurations are possible and within the scope of this disclosure, three exemplary arrangements of electrodes 180 providing two ECG leads X and Y providing two channels of ECG data are shown. FIG. 2A provides an exemplary electrode arrangement of four electrodes 180 configured into transverse groups, the ECG electrodes 180 form a horizontal lead arrangement 102*x* and a vertical lead arrangement 102*y*, with each lead generating a respective channel X and Y of ECG data. FIG. 2B provides a similar output of a horizontal lead arrangement 102*x* and a vertical lead arrangement 102*y*, but utilizing only tree electrodes instead of four as shown in FIG. 2A. In the embodiment of FIG. 2B, the horizontal lead arrangement 102*x* shares an electrode with the vertical lead arrangement 102*y*. FIG. 2C exemplifies a third lead arrangement comprising three electrodes, where both the lead arrangements 102*x* and 102*y* extend horizontally, but for different distances and thus capturing different vectors through the heart. The ECG electrodes 180 are connected to an ECG receiver 181 that transfers the obtained ECG potential to the physiological acquisition controller 155 for processing, including R-peak reference data generation and R-peak detection. In various embodiments, the connection between the electrodes 180 and the ECG receiver 181 may be by any known means, including traditional wired connection or by wireless transmission.

Figure 3:
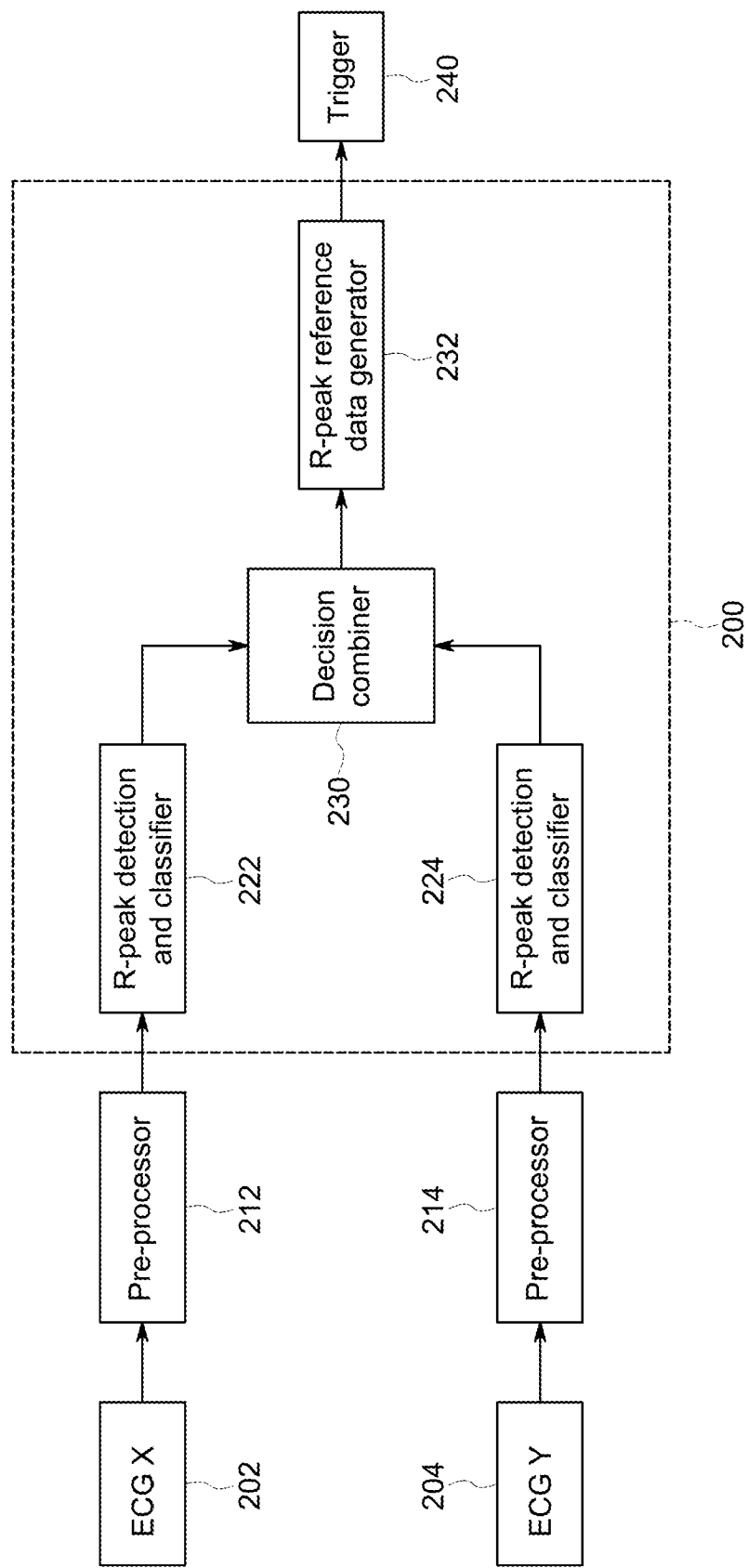
FIG. 3 is a block diagram illustrating a process flow for generating R-peak reference data for use in triggering MR image data acquisition.

FIG. 3 is a block diagram illustrating a process flow for triggering MR data acquisition based on two channels of ECG data, such as acquired via the electrode arrangements exemplified in FIGS. 2A-2C. A first portion of the process flow includes collection and provision of two ECG datasets, including via a first ECG channel 202 and a second ECG channel 204, and pre-processing each ECG dataset via pre-processors 212 and 214 each processing a channel. The preprocessing may include, for example, filtering and/or amplification steps. For example, pre-processing may include applying a high pass filter, (e.g., a 1 Hertz high pass filter), and a low pass filter, (e.g., a 35 Hertz low pass filter). In other embodiments, the filtering frequencies may be adjusted and/or different filtering steps executed in order to respond to noise in a particular environment. For example, the physiological acquisition controller 155 may be utilized in the initialization stages for the acquisition and pre-processing of the ECG datasets.

The ECG datasets are then processed by the R-peak detector 200 to detect R-peaks and generate R-peak reference data. The R-peak detector 200 may be software (e.g., a set of computer executable instructions), hardware, firmware, or any combination thereof, for processing ECG data to detect R-peaks and generate R-peak reference data for using in cardiac gating, i.e., for triggering MR data acquisition. In the embodiment of FIG. 1, the R-peak detector 200 is implemented as part of the physiological acquisition controller 155. In other embodiments, the R-peak detector 200 may be implemented elsewhere in the system 100, and may be distributed across multiple computing and/or control aspects or elements of the system 100. The R-peak detector 200 performs R-peak detection steps and reference data generation, and may includes one or more sub-components, including for example R-peak detection and classifiers 222 and 224, a decision combiner 230 that combines the outputs of the R-peak detection and classifiers, and an R-peak reference data generator 232 that generates appropriate R-peak reference data accordingly. Further, a trigger generator 240 that generates the trigger for MR image data acquisition is included in the system 100.

The process flow to identify QRS complexes within the derived waveform and generate reference data accordingly is utilized for processing both the initial ECG dataset obtained from the patient prior to moving the patient into the bore, and the reference ECG dataset obtained once the patient is positioned in the bore. As will be exemplified in more detail with respect to subsequent Figures, the initial ECG dataset is processed in order to generate initial R-peak reference data and generate initial triggers accordingly. The initial triggers, while not used as image triggers, may nonetheless be displayed on the display 118 to indicate to a clinician that the system 100 is functioning properly and the adequate reference data is thus far obtainable based on the initial ECG data being collected. This signals, for example, that the electrodes are adequately attached to the patient. The initial peak reference data is also stored and utilized for subsequent processing of the reference ECG dataset, which is the dataset acquired once the patient is positioned within the bore 146. Namely the R-peak classifiers 222 and 224 are configured to utilize the initial R-peak reference data in processing the reference ECG dataset.

Depending on the system 100 configuration for triggering acquisition of MR image data, the R-peak reference data may be formatted differently to provide R-peak data in a relevant and usable format. For example, in vectocardiogram (VCG) the R-peak reference data provides morphological templates for use in image triggering. VCG is a known technique for cardiac gating, one example of which is described in U.S. Pat. No. 7,738,943 which is hereby incorporated by reference in its entirety. In such an embodiment, the R-peak reference data for VCG may be a group of short time series of data samples centered around and corresponding to the R-peaks.

Figure 4:
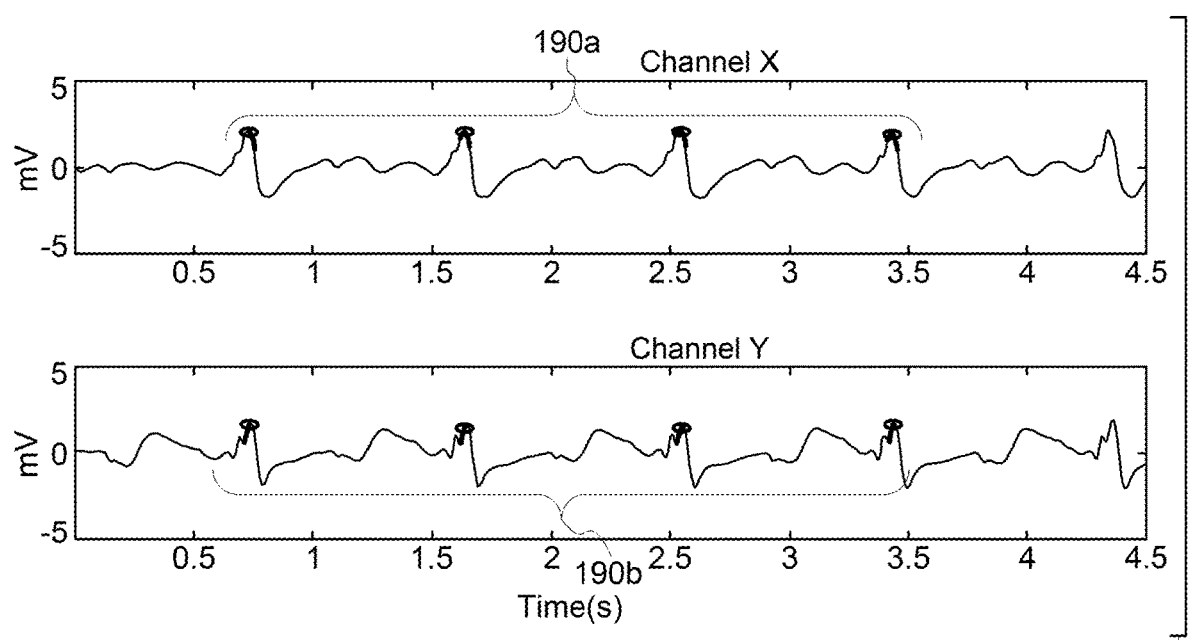
FIG. 4 is a graph illustrating an exemplary ECG dataset comprising two channels of ECG data.

FIG. 4 provides an exemplary ECG dataset, which could be an initial ECG dataset or a reference ECG dataset. In the example, the ECG dataset is a 4.5 second segment of two channels of ECG data. The ECG dataset, or data segment, is processed in order to identify a set of R-peaks in each channel X and Y of ECG data. In the example, each set of R-peaks 190a, 190b includes four peaks. Phase adjustment has been performed such that the sets of R-peaks 190a and 190b are time-correlated. In various embodiments, a continually moving time window of ECG data may be acquired and processed. Preferably, the time window of ECG data is sufficiently long to include three or more QRS complexes, or heartbeats. In the example, a 4.5 second time window is utilized, which continuously updates every 500 milliseconds. In other embodiments, the ECG time window may be shortened to, for example, 4 seconds, or lengthened to 5 seconds or more. In each time window, ECG data is processed to determine whether R-peaks can be adequately detected, such as detection of at least three R-peaks with a threshold confidence level, or likelihood of accuracy.

Figure 5:
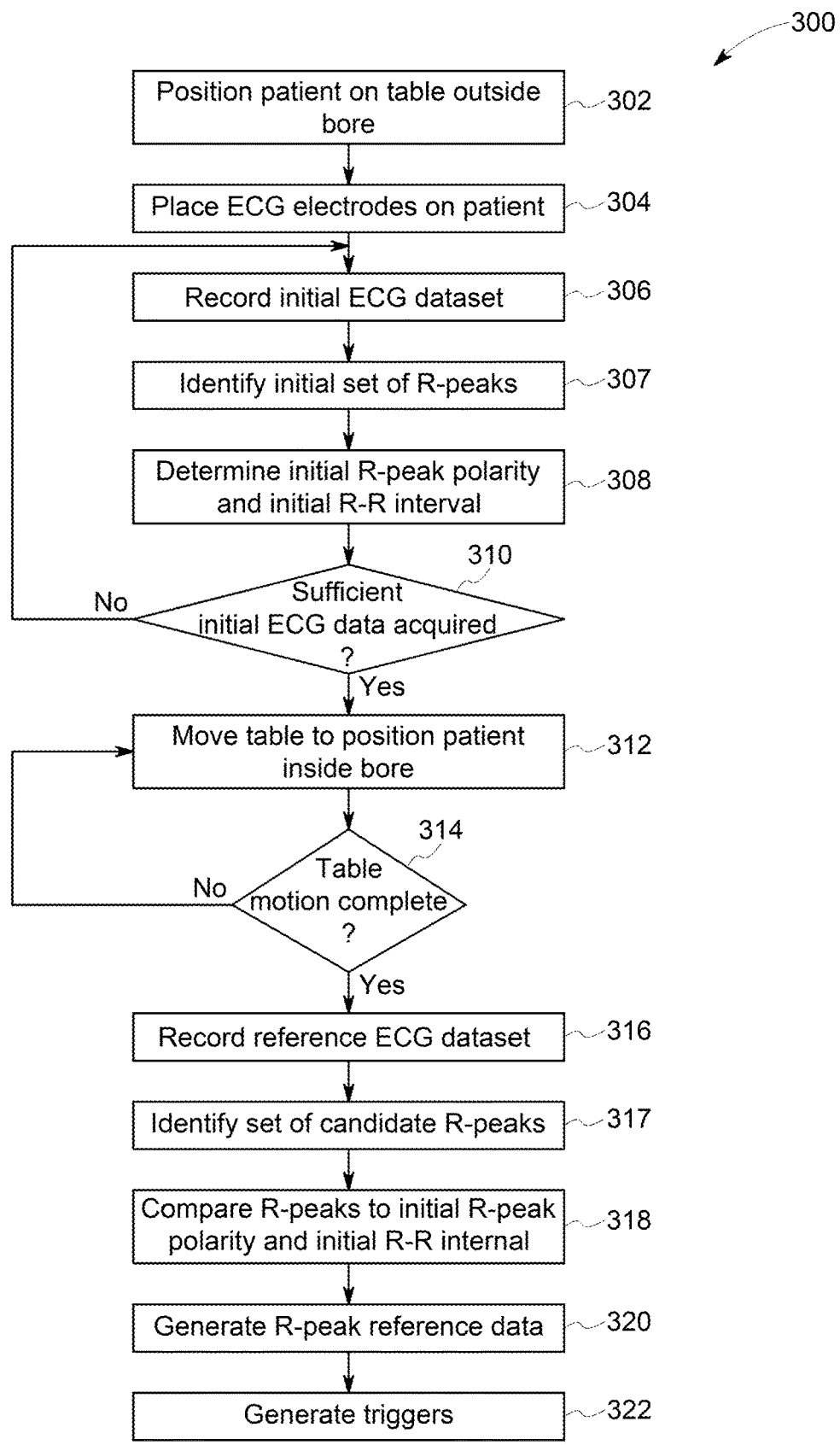
FIG. 5 is a flow chart exemplifying one embodiment of a method of generating ECG reference data for MR image data acquisition.

FIG. 5 exemplifies one embodiment of such a method of generating ECG reference data, including R-peak detection. In the depicted example, a patient is positioned on the table outside of the bore at step 302 and ECG electrodes are placed on the patient at step 304. For example, three or four electrodes may be placed on the patient in accordance with the examples at FIGS. 2A-2C. An initial ECG dataset is obtained at step 306 and initial R-peak characteristics, including an initial R-peak polarity and initial R-R interval, are determined based on the initial dataset at step 308. Such polarity and R-R interval determinations are made based on an initial set of R-peaks detected within the initial ECG dataset. Step 310 may be executed to determine whether sufficient initial ECG data is acquired. For example, an alert may be generated if initial R-peak polarity and initial R-R interval determinations are unable to be made for each of the at least two available channels of ECG data. For example, if one or more of the electrodes 180 are poorly placed on the patient, then an alert may be generated to advise a clinician to replace the electrode so that an adequate initial ECG dataset can be obtained wherein initial R-peak polarity and initial R-R interval information can be determined for each of the two channels of ECG data. Alternatively or additionally, analysis to determine whether sufficient ECG data has been acquired may require acquisition of at least a threshold number of R-peaks, a threshold number of sets of R-peaks, or a threshold duration of ECG data for which valid sets of R-peaks are identified.

Once sufficient initial ECG data is acquired, the patient is moved into the bore. In certain examples, the R-peak detector 200 is configured to automatically determine when sufficient initial ECG data is acquired and to interact with the patient positioning system 147 to automatically move the patient into the bore once initial acquisition is complete. Namely, the table 171 of the MRI device is moved to position the patient within the bore 146. Once the positioning is complete and the table is no longer moving, as determined at step 314 (such as via information provided by the patient positioning system 147), a reference ECG dataset is obtained at step 316. Thereby, the reference ECG dataset can be acquired once the patient positioning is complete, and thus interference from the motors moving the table 171 will be avoided, and prior to initiating the MR scan. Each reference ECG dataset is analyzed to detect R-peaks, which are compared to the initial R-peal polarity and initial R-R interval at step 318. R-peak reference data is generated at step 320 based on the R-peaks identified in the reference ECG dataset.

Thereby, the R-peak reference data accounts for interference by the MRI device on the ECG waveforms, including accounting for the MHD effects of the magnetic field on the ECG waveforms. Moreover, the R-peak reference data accounts for the patient's disease characteristics within the ECG waveforms being obtained and any other consistent situational effect (e.g., due to patient position) on the ECG waveforms. Additionally, R-peak detection in the reference ECG dataset accounts for the polarity and relative amplitude and slope expected in each respective channel of ECG data, which is determined based on the initial ECG dataset. In certain embodiments described herein below, methods may also include channel rejection of data where R-peak detection is not reliable, thereby relying on a remaining one or more reliable channels and eliminating the unreliable R-peak detection information from the reference data. Additionally, where more than one channel of ECG data is utilized for the R-peak reference data, phase adjustments may be applied to align the peaks in each of the channels to provide consistent information across all channels of ECG data utilized in the R-peak reference data. The R-peak reference data is then utilized to generate triggers at step 322, which are implemented for triggering acquisition of the MR data from the subject, which is performed in accordance with known methods in the field of MR imaging.

Figure 6A:
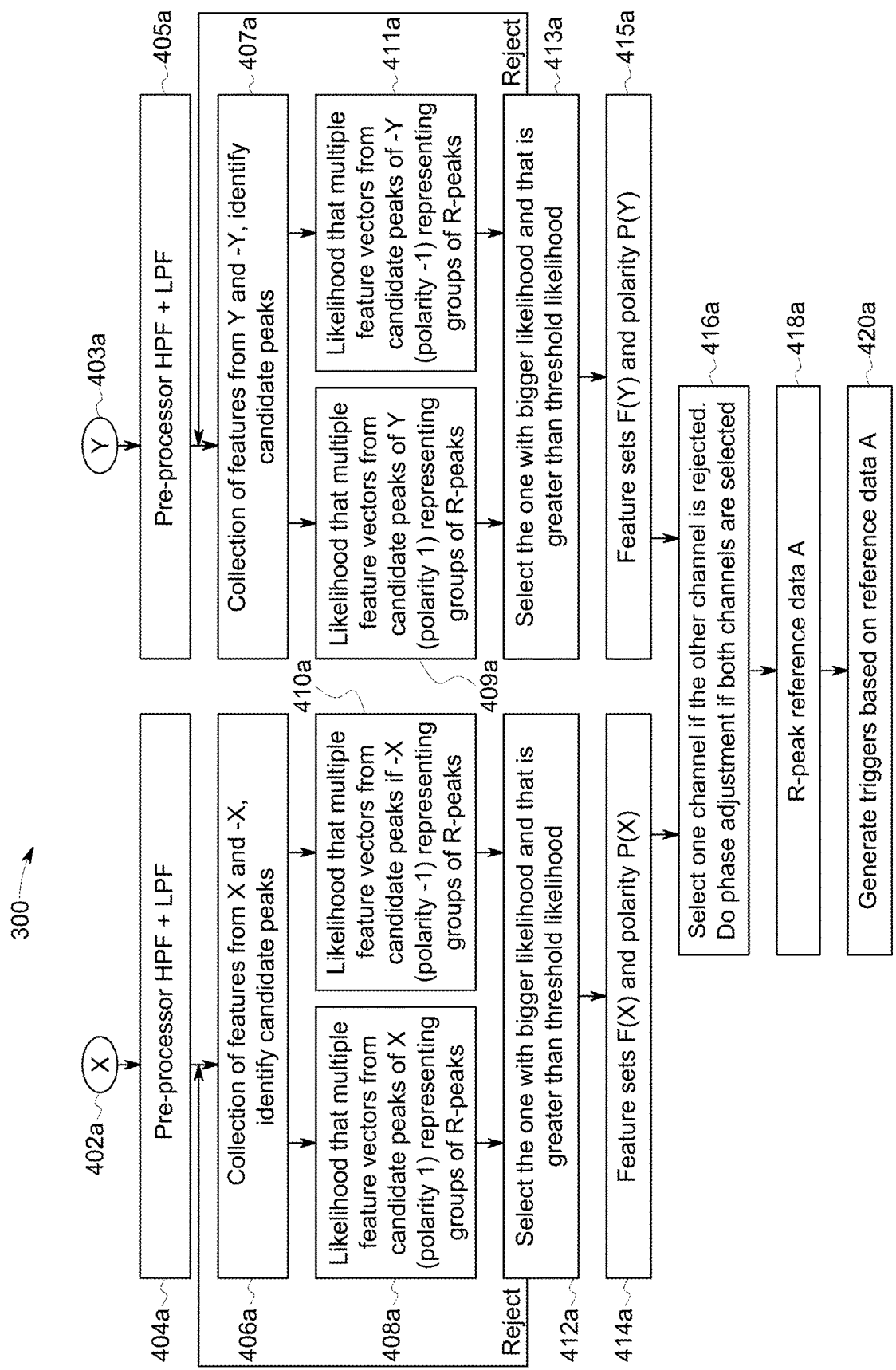
FIGS. 6A and 6B are flow charts exemplifying additional exemplary embodiments of methods, or portions thereof, of generating ECG reference data for MR image data acquisition.
Figure 6B:
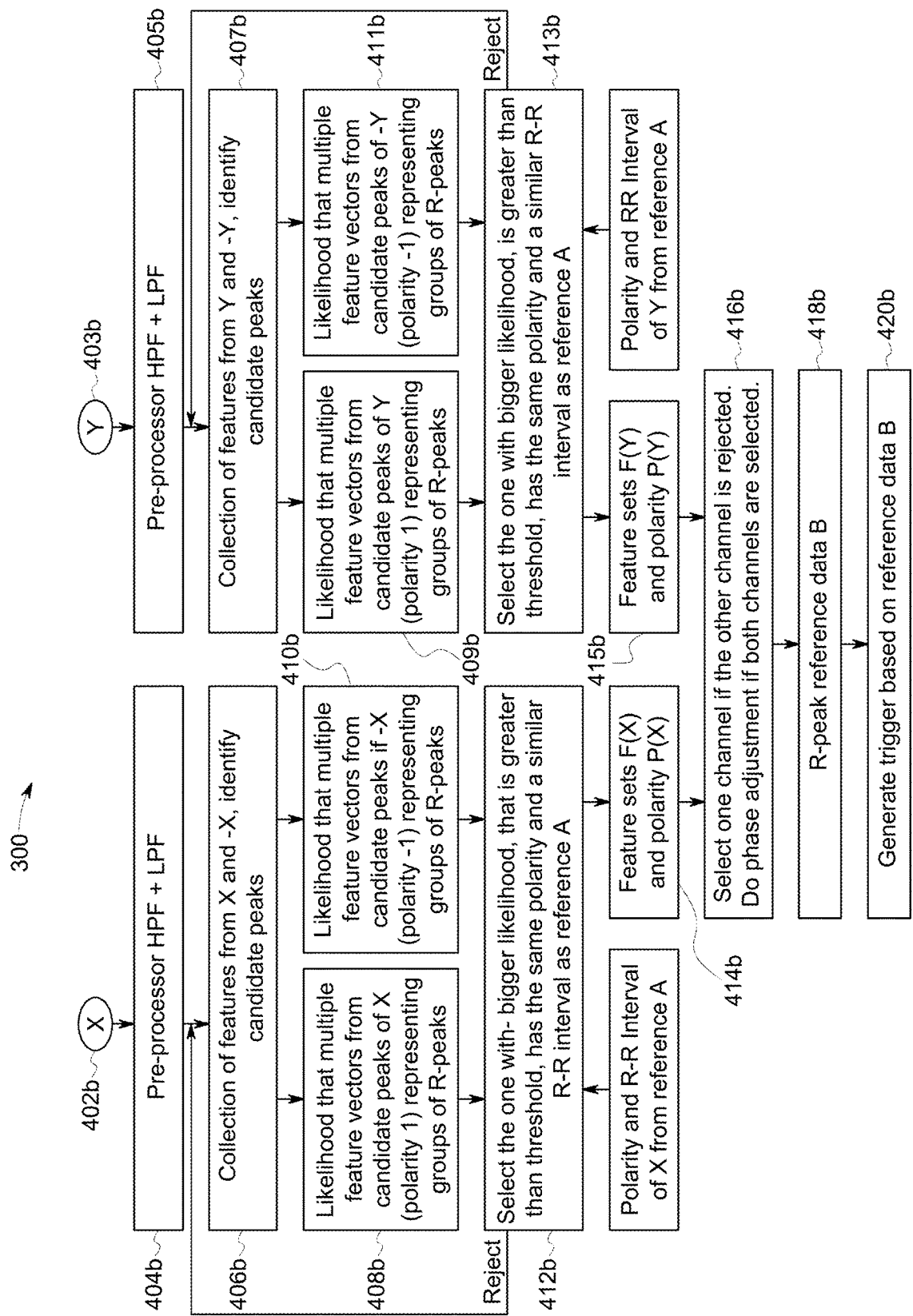

FIGS. 6A and 6B depict exemplary methods of processing ECG datasets to generate R-peak reference data, where FIG. 6A depicts steps for generating initial R-peak reference data (i.e., R-peak reference data A) from an initial ECG dataset (provided at initial steps 402a and 403a) and FIG. 6B depicts corresponding method steps for generating final R-peak reference data (i.e. R-peak reference data B) based on a reference ECG dataset acquired from the patient when the patient is positioned inside the bore 146 (provided at initial steps 402b and 403b). In both exemplary methods, each two-channel ECG dataset is pre-processed (steps 404a-b and 405a-b) and candidate peaks are identified (steps 406a-b and 407a-b) in each channel X and Y. For example, candidate peaks may be identified by identifying relative minimums and maximums that meat certain threshold criteria, such as for amplitude and slope. For example, a set of positive candidate peaks and a set of negative candidate peaks may be identified for each channel, where each candidate peak has a relative amplitude within a threshold amplitude range and a slope within a threshold slope range.

At steps 408a-411a, analysis is performed to determine a likelihood (e.g., a combined likelihood as described below) that each of the set of positive and negative candidate peaks represents an actual group of R-peaks, for each channel X and Y. Between the negative candidate peaks and the positive candidate peaks, the one with the bigger likelihood is selected at steps 412a-413a for each channel X and Y, and the likelihood for the selected set of R-peaks is compared to a threshold likelihood value (e.g., a threshold combined likelihood). If the likelihood value is less than the threshold, then the set of candidate peaks is rejected in that channel. If the likelihood exceeds the threshold, then the set of R-peaks is affirmed and R-peak reference data is generated for the respective channel of ECG data, including feature information about the R-peaks (e.g. amplitude, slope, and R-R interval, and the polarity of the R-peaks).

At steps 414a and 415a, R-peak information (e.g., feature sets and polarity) is generated for each channel X and Y, which will be discussed in detail below.

If neither channel is rejected, the data from both channels can be correlated into a set of initial R-peak reference data at steps 416a-418a. This includes adjusting the phase of one or more of the channel data so that the R-peaks represented in each of the channels are aligned. Due to placement of the electrodes, there can be a phase difference between the features in the data channels, e.g., which can be anywhere from 0 to 30 milliseconds. Appropriate phase adjustment is made at step 416a, and R-peak reference dataset A is outputted at step 418a. If one of the channels is rejected, the other channel is selected as the R-peak reference dataset A and outputted at step 418a. Step 420a is executed to generate triggers based on the R-peak reference data A. Depending on the trigger logic used by the system, the R-peak reference data is provided in different formats. For example, as described above, the R-peak reference data may be a group of short time series of data samples centered as R-peaks in VCG systems.

FIG. 6B depicts a corresponding method of R-peak detection for the reference set of ECG data, which parallels the method steps depicted in FIG. 6A for the initial set of ECG data except that the steps in FIG. 6B for processing the reference set of ECG data includes analysis based on the characteristics of the initial R-peak reference data, such as initial R-peak polarity and initial R-R interval. Specifically, steps 412b and 413b select or reject the reference set of R-peaks for each channel X and Y based on whether the set with the larger likelihood has the same polarity as the initial polarity and has a similar R-R interval as the initial R-R interval. If any of those conditions are not true, then the reference set of R-peaks for that channel is rejected. For example, a threshold interval range may be set based on the initial R-R interval, and the selected set of R-peaks may be rejected if the peak-to-peak intervals do not fall within that threshold interval range. In certain examples, the peak-to-peak intervals of the selected R-peak data may each be compared to the threshold, or a mean peak-to-peak interval value may be determined and compared to the threshold.

Figure 7:
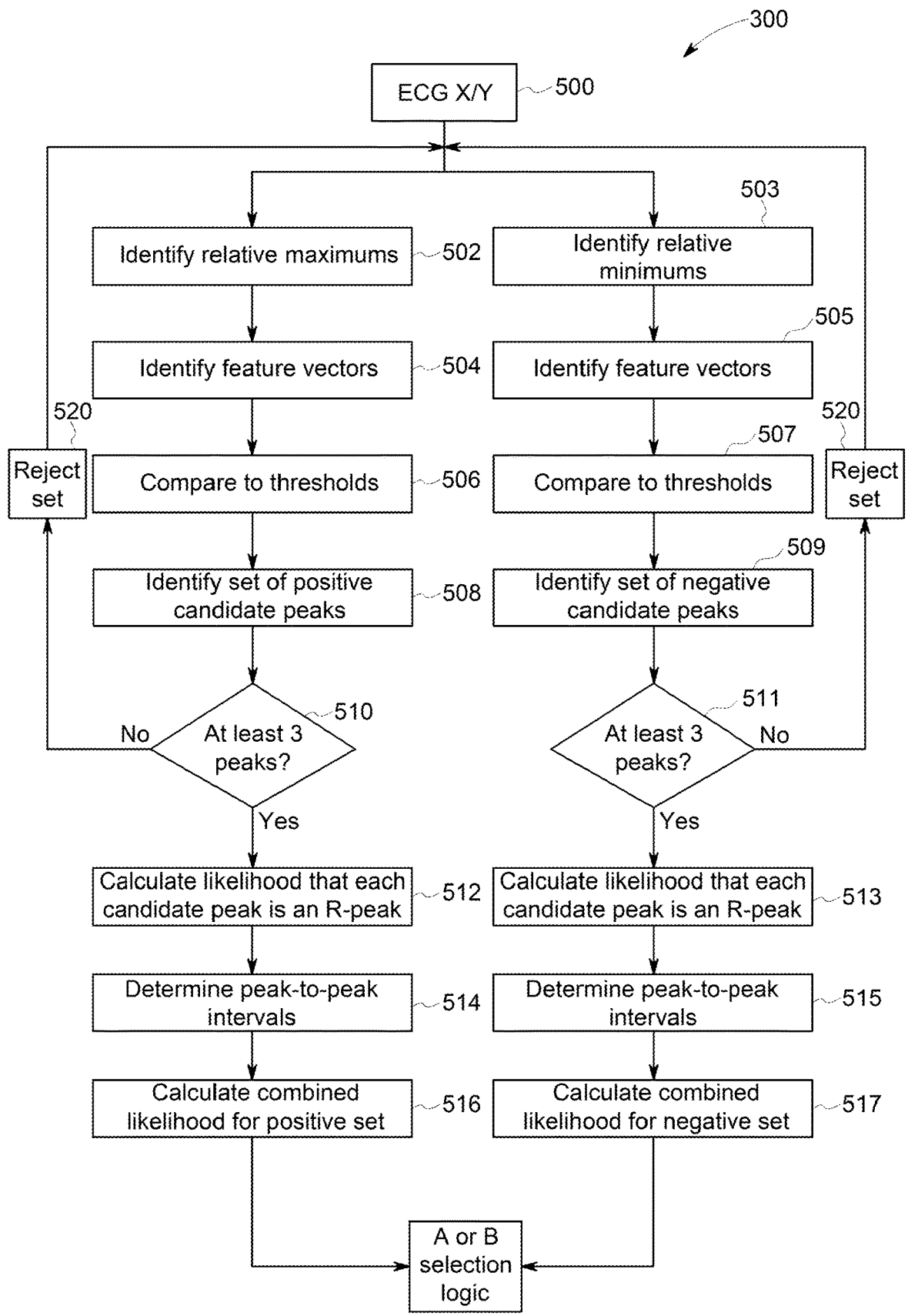
FIGS. 7 and 8A-8B are flow charts exemplifying further embodiments of methods, or portions thereof, of generating ECG reference data for MR image data acquisition.
Figure 8A:
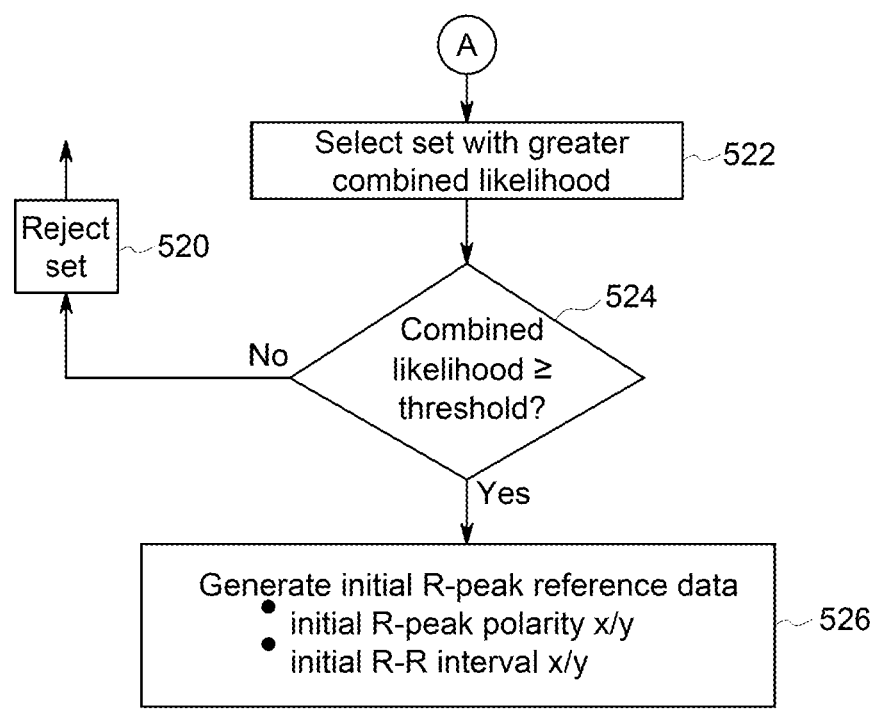
Figure 8B:
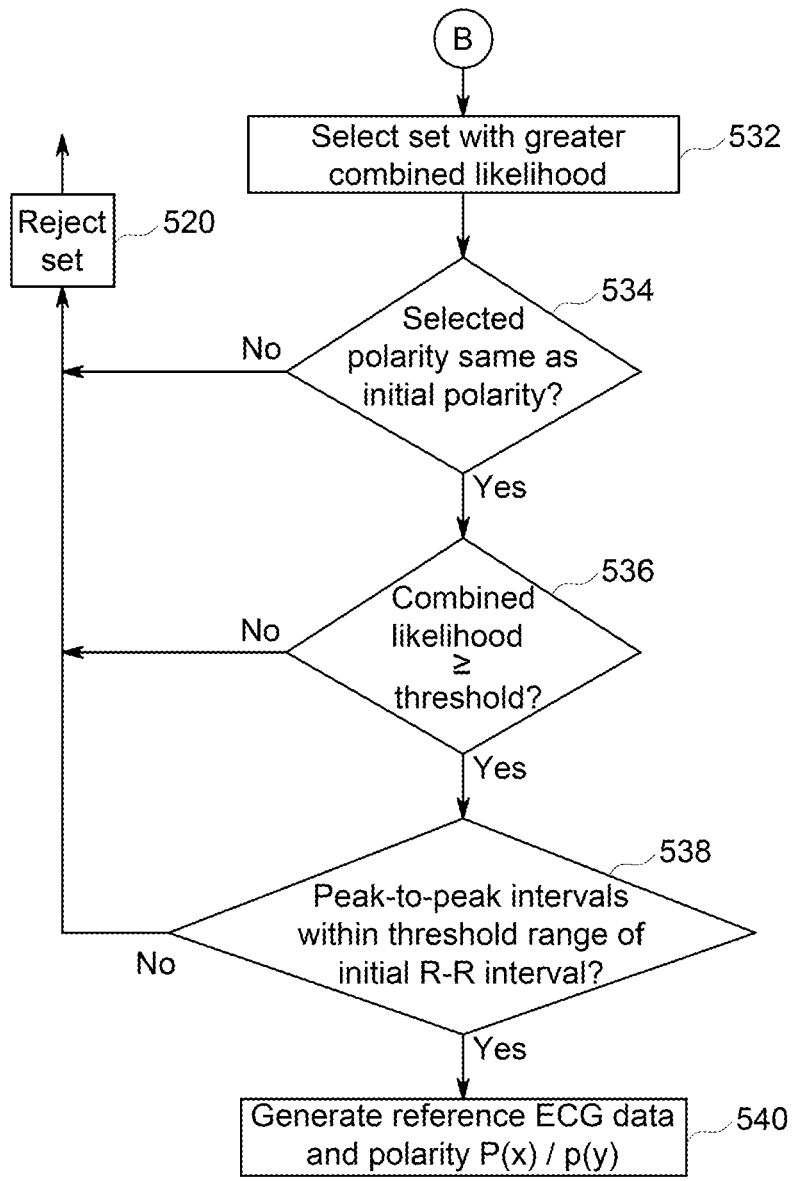

FIGS. 7 and 8A-8B depict additional embodiments of methods 300, or portions thereof, for generating ECG reference data in accordance with the present disclosure. FIG. 7 depicts steps of R-peak detection and likelihood calculation that may be executed across each channel of ECG data and for each of the initial ECG dataset and the reference ECG dataset. FIG. 8A depicts exemplary steps that may be executed for selecting the initial set of R-peaks and generating the initial reference ECG data based on the initial ECG dataset. FIG. 8B depicts exemplary method steps for selecting the reference set of R-peaks based on characteristics of the initial reference data such as the initial R-peak polarity and the initial R-R interval, and generating the final R-peak reference data accordingly.

In FIG. 7, a respective channel of ECG data, either X or Y is received at step 500. The respective channel of the ECG dataset is the processed according to the depicted steps. Each channel of ECG data is separately processed according to the depicted set of steps; however, the steps are shown only once in the figures for the sake of brevity and clarity. For each time segment of ECG data in each channel X and Y, maximums of relative amplitude (also called relative maximums) are identified at step 502 and minimums of relative amplitude (also called relative minimums) are identified at step 503. These are local maximums and minimums identified in running time segments of the ECG data. At the local maximums, the first derivative is 0 and the second derivative is negative. At the local minimums, the first derivative is 0 and the second derivative is positive. In one exemplary embodiment, a 16 millisecond window on either side of each value in the dataset is analyzed to identify any relative maximums or minimums therein.

For each identified relative maximum point and minimum point, a feature vector is determined at steps 504 and 505. The feature vector is comprised of values describing the relative maximum or minimum. In one embodiment, the feature vector includes a left relative amplitude, a right relative amplitude, a left slope, and a right slope. Left and right refer to forward and backward in time to the peak position. Left and right relative amplitudes may be defined as the distance from the peak to the respective left and right inflection points normalized to one millivolt per unit. Left and right slopes may be defined as the slope between the peak point and the left and right inflection point, normalized using a heuristic unit slope. The values in the feature vectors are compared to corresponding thresholds at steps 506 and 507. In certain embodiments, the thresholds are determined based on data from multiple different patients. The patient data utilized for calculating the thresholds may preferably include patients across a wide variety of demographics and representing a multitude of cardiac conditions and the ECG manifestations thereof. Furthermore, the multi-patient data utilized to calculate the thresholds preferably represents ECG data influenced by a range of magnetic field strengths, including but not limited to 1.5 Tesla, 3 Tesla, and 7 Tesla. Thereby, the thresholds can effectively account for the various conditions and cardiac disease manifestations that may arrive in patients undergoing cardiac MRI's. A set of positive candidate peaks is identified at step 508 as those relative maximums having feature vectors within the threshold range as determined at step 506. Similarly, a set of negative candidate peaks is identified at step 509 as those relative minimums having feature vectors within the threshold range as determined at step 507. Steps 510 and 511 are conducted to determine whether at least three peaks are identified in each of the set of positive candidate peaks and the set of negative candidate peaks. If at least three positive peaks are not identified at step 510, then the set of positive candidate peaks is rejected at step 520. If at least three negative peaks are not detected at step 511, then the set of negative candidate peaks is rejected at step 520.

A likelihood analysis is then conducted for each of the remaining positive set of candidate peaks and negative set of candidate peaks. At step 512, a likelihood value is calculated for each candidate peak in the set of positive candidate peaks, wherein the likelihood value represents a likelihood that each candidate peak is an actual R-peak. Similarly, a likelihood value is calculated for each negative candidate peak at step 513. In one embodiment, the likelihood analysis assumes that the feature vector of each candidate peak is a Gaussian random process of independent component, where a monotonic function of the likelihood that a particular candidate peak represents a single R-peak can be expressed as:

$$\sum_{i=1}^{4} \frac{x_i m_i}{\sigma_i^2}$$

where $m_i$ is the mean and $\sigma_i$ is the variance for each component, which include $x_1$ equals left relative amplitude, $x_2$ equals right relative amplitude, $x_3$ equals left slope, and $x_4$ equals right slope. An approximation of this monotonic function of likelihood may be instead utilized, as:

LikelihoodS=min(left_amp,right_amp)+min(left_slope,right_slope)

where the min operator is used to select the worst case between the left and right amplitude (i.e., using the smaller value to represent the amplitude feature), and the minimum left and right slope, and wherein the mean and variance scaler has been adjusted using the heuristic unit slope relative to millivolt unit amplitude.

A combined likelihood may then be calculated representing the likelihood that the relevant set of candidate peaks (whether the positive or negative set) represents an actual group of R-peaks. The combined likelihood can then be approximated based on the likelihood for each candidate peak. The combined likelihood that the set of candidate peak represents an actual group of R-peaks is inversely proportional to the variance of each of the features across the multiple candidate peaks. In certain embodiments a peak-to-peak interval between the selected set of R-peak may also be determined (steps 514 and 515) accounted for in the likelihood calculation, adding a fifth feature to the feature vector for each peak, where $x_5$=peak-to-peak interval. The combined likelihood may then be approximated for each channel at steps 516 and 517 as:

LikelihoodM=mean(LikelihoodS)+0.2/$\Sigma_{i=1}^{5}\sigma_i$ where $\sigma_i$ represents an approximation of the variance of feature $x_i$ across the five (N=1-5) candidate peaks and 0.2 is a weight factor. The approximation of the variance $\sigma_i$ may be defined as:

$\sigma_i$=((max($x_i$)−min($x_i$))/mean($x_i$))/(numPeaks−1)

Accordingly, the change in the feature component across the candidate peaks is relative to the mean of the feature component $x_i$, which is averaged against the number of peaks minus 1.

Steps are then executed to select a set of R-peaks, which may be an initial set of R-peaks if analyzing the initial ECG dataset (FIG. 8A) or the reference set of R-peaks if analyzing the reference ECG dataset (FIG. 8B). The set of R-peaks are selected as either the set of positive candidate peaks or the set of negative candidate peaks based on which set of candidate peaks has the greater combined likelihood, as represented in step 522 of FIG. 8A. The combined likelihood of the selected set is then compared to a threshold combined likelihood at step 524. In certain embodiments, the threshold combined likelihood may be predetermined based on the set of multi-patient data described above for determining the feature vector thresholds. If the combined likelihood does not meet or exceed the threshold, then the set of R-peaks is rejected at step 520. Assuming the threshold is met or exceeded, then initial R-peak reference data is generated at step 526. The initial R-peak polarity and the initial R-R interval are also generated for each channel X and Y. The initial values are then utilized in processing the reference ECG dataset as exemplified in FIG. 8B.

As shown in FIG. 8B exemplifying method steps for selecting the reference set of R-peaks from the reference ECG dataset, the set with the greater combined likelihood is selected at step 532. Step 534 is executed to determine whether the polarity of the selected set matches the initial R-peak polarity for the corresponding channel X or Y. If the polarity does not match, then the selected reference set is rejected at step 520. The combined likelihood of the selected reference set of R-peaks is then compared to a threshold combined likelihood at step 536, and the reference set of R-peaks is rejected if the combined likelihood is less than the threshold. The peak-to-peak intervals of the reference set of R-peaks are then compared to the initial R-R interval data for the corresponding channel to determine at step 538 whether the peak-to-peak intervals are within a threshold range of the initial R-R interval. If not, then the reference set of R-peaks are rejected. If all qualification analysis at steps 534-538 are positive, then the reference ECG data is generated at step 540 based on the reference set of R-peaks. It should also be recognized that if multiple channels of R-peak data are selected, then phase adjustment is conducted and both selected channels of R-peaks are included in the relevant R-peak reference data generated at steps 526 and 540.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

I claim:

1. A method of generating electrocardiogram (ECG) reference data for magnetic resonance (MR) image data acquisition with a magnetic resonance imaging (MRI) device, the method comprising:
   obtaining an initial ECG dataset from a patient on a table of the MRI device prior to moving the patient into a bore of the MRI device, wherein the initial ECG dataset comprises at least two channels of ECG data;
   identifying an initial set of R-peaks in the initial ECG dataset obtained prior to moving the patient into the bore and determining initial R-peak characteristics for at least one of the at least two channels of the initial ECG dataset;
   obtaining a reference ECG dataset from the patient once the patient is positioned in the bore, wherein the reference ECG dataset comprises the at least two channels of ECG data;
   identifying a reference set of R-peaks in the reference ECG dataset based on the initial R-peak characteristics, including:
   identifying a set of positive candidate peaks for each channel as three or more relative maximums with at least one of a relative amplitude within a threshold amplitude range and a slope within a threshold slope range;
   identifying a set of negative candidate peaks for each channel as three or more relative minimums with at least one of a relative amplitude within the threshold amplitude range and a slope within the threshold slope range;
   calculating a combined likelihood that the set of positive candidate peaks represents an actual group of R-peaks and a combined likelihood that the set of negative candidate peaks represents the actual group of R-peaks based on the initial R-peak characteristics; and
   selecting the set with the greatest combined likelihood as the reference set of R-peaks;
   generating R-peak reference data based on the reference set of R-peaks; and
   triggering acquisition of MR image data from the patient using the R-peak reference data.

2. The method of claim 1, further comprising rejecting the set of positive candidate peaks or the set of negative candidate peaks if the combined likelihood is less than a threshold combined likelihood.

3. The method of claim 1, further comprising:
   calculating a likelihood for each candidate peak in the set of positive candidate peaks and each candidate peak in the set of negative candidate peaks that each respective candidate peak represents an actual R-peak;
   wherein the likelihood that each candidate peak represents an actual R-peak is based on at least one of a relative amplitude of the candidate peak and a slope of the candidate peak; and
   calculating each combined likelihood based on the likelihoods for the candidate peaks in the respective set of positive candidate peaks or set of negative candidate peaks.

4. The method of claim 1, further comprising:
   determining a peak-to-peak interval between each of the candidate peaks; and
   calculating each combined likelihood based further on the peak-to-peak intervals in the respective set of positive candidate peaks or set of negative candidate peaks.

5. The method of claim 1, wherein each combined likelihood is calculated based on a variance in at least one of a relative amplitude of the candidate peaks, a slope of the candidate peaks, and a peak-to-peak interval of the candidate peaks in the respective set of positive candidate peaks or set of negative candidate peaks.

6. The method of claim 1, further comprising generating a feature vector for each candidate peak, wherein the feature vector includes a left relative amplitude, a right relative amplitude, a left slope, and a right slope for the respective candidate peak.

7. The method of claim 6, further comprising:
   comparing the left relative amplitude, the right relative amplitude, the left slope, and the right slope of each feature vector to a corresponding set of thresholds; and
   identifying a set of positive candidate peaks and a set of negative candidate peaks based on the comparisons.

8. The method of claim 1, wherein the R-peak characteristics include an initial R-peak polarity and an initial R-R interval; and
   wherein the reference set of R-peaks are identified in each of the at least two channels of ECG data in the reference ECG dataset based on the initial R-peak polarity and the initial R-R interval for the corresponding channel in the initial ECG dataset.

9. The method of claim 1, further comprising:
   determining that no initial set of R-peaks is identifiable in one of the at least two channels of the initial ECG dataset; and ignoring the corresponding channel in the reference ECG dataset and generating the R-peak reference data based only on one or more remaining channels of the reference ECG dataset.

10. A MRI device comprising:
a bore;
a table configured to support a patient and movable to move the patient in and out of the bore; and
a controller configured to:
  obtain an initial electrocardiogram (ECG) dataset acquired by an ECG acquisition system from a patient on a table of the MRI device prior to moving the patient into a bore of the MRI device, wherein the initial ECG dataset comprises the at least two channels of ECG data;
  identify an initial set of R-peaks in the initial ECG dataset obtained prior to moving the patient into the bore, and determine initial R-peak characteristics for at least one of the at least two channels of the initial ECG dataset;
  obtain a reference ECG dataset acquired by the ECG acquisition system from the patient once the patient is in the bore of the MRI device, wherein the reference ECG dataset comprises the at least two channels of ECG data;
  identify a reference set of R-peaks in the reference ECG dataset based on the initial R-peak characteristics including:
  identify a set of positive candidate peaks for each channel as three or more relative maximums with at least one of a relative amplitude within a threshold amplitude range and a slope within a threshold slope range;
  identify a set of negative candidate peaks for each channel as three or more relative minimums with at least one of a relative amplitude within the threshold amplitude range and a slope within the threshold slope range;
  calculate a combined likelihood that the set of positive candidate peaks represents an actual group of R-peaks and a combined likelihood that the set of negative candidate peaks represents the actual group of R-peaks based on the initial R-peak characteristics; and
  select the set with the greatest combined likelihood as the reference set of R-peaks;
  generate R-peak reference data based on the reference set of R-peaks, wherein the R-peak reference data is formatted for use in triggering MR image data acquisition.

11. The MRI device of claim 10, wherein the controller is further configured to:
  reject the set of positive candidate peaks or the set of negative candidate peaks if the combined likelihood is less than a threshold combined likelihood;
  wherein each combined likelihood is calculated based on a variance in at least one of a relative amplitude of the candidate peaks, a slope of the candidate peaks, and a peak-to-peak interval of the candidate peaks in the respective set of positive candidate peaks or set of negative candidate peaks.

12. The MRI device of claim 10, further comprising:
  wherein the controller is further configured to automatically obtain the initial ECG dataset prior to movement of the table to position the patient inside the bore, and automatically obtain the reference ECG dataset after movement of the table to position the patient inside the bore is complete and prior to beginning an MR scan.

* * * * *